(12) United States Patent
Takeuchi et al.

(10) Patent No.: US 9,138,550 B2
(45) Date of Patent: Sep. 22, 2015

(54) NON-HEATING TOBACCO FLAVOR SUCTION DEVICE

(75) Inventors: Manabu Takeuchi, Tokyo (JP);
Michihiro Inagaki, Yokohama (JP);
Morio Yajima, Yokohama (JP);
Kazuhiko Katayama, Yokohama (JP);
Atsuro Yamada, Yokohama (JP);
Manabu Yamada, Yokohama (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 13/214,479

(22) Filed: Aug. 22, 2011

(65) Prior Publication Data
US 2011/0297166 A1 Dec. 8, 2011

Related U.S. Application Data

(63) Continuation of application No. PCT/JP2010/052369, filed on Feb. 17, 2010.

(30) Foreign Application Priority Data

Feb. 23, 2009 (JP) ................. 2009-039380

(51) Int. Cl.
*A24F 47/00* (2006.01)
*A61M 15/06* (2006.01)
(52) U.S. Cl.
CPC .............. *A61M 15/06* (2013.01); *A24F 47/002* (2013.01)
(58) Field of Classification Search
CPC .............................. A61M 15/06; A24F 47/006
See application file for complete search history.

(56) References Cited

U.S. PATENT DOCUMENTS

| | | | | |
|---|---|---|---|---|
| 3,403,202 A | * | 9/1968 | Green et al. ................. | 264/404 |
| 3,470,883 A | * | 10/1969 | Shepherd et al. ............. | 131/332 |
| 4,624,269 A | | 11/1986 | Story et al. | |
| 4,938,236 A | * | 7/1990 | Banerjee et al. ............. | 131/194 |
| 5,159,940 A | | 11/1992 | Hayward et al. | |
| 6,532,965 B1 | | 3/2003 | Abhulimen et al. | |
| 2007/0000505 A1 | * | 1/2007 | Zhuang et al. ................ | 131/342 |
| 2007/0186941 A1 | | 8/2007 | Holton, Jr. | |
| 2008/0053465 A1 | * | 3/2008 | Tarora et al. .................. | 131/187 |

FOREIGN PATENT DOCUMENTS

| | | |
|---|---|---|
| CA | 2252814 A | 11/1997 |
| CA | 2147260 A | 4/1999 |
| CN | 101128130 A | 2/2008 |
| CN | 101254025 A | 9/2008 |
| EP | 1 656 842 A1 | 5/2006 |
| EP | 1 859 694 A1 | 11/2007 |

(Continued)

OTHER PUBLICATIONS

Smoke Filtration Filter Design, Philip Morris, 2002, accessed on Mar. 8, 2012: http://legacy.library.ucsf.edu/tid/hro25c00.*

(Continued)

*Primary Examiner* — Michael J Felton
(74) *Attorney, Agent, or Firm* — Birch, Stewart, Kolasch & Birch, LLP

(57) ABSTRACT

A non-heating tobacco flavor suction device (1) comprises a suction holder (2) with a suction path defined inside and a filler (8) arranged in the suction path. The filler (8) is formed of tobacco particles. The suction path and the filler (8) arranged therein provide a ventilation resistance of between about 40 and about 80 mmAq in cooperation with each other.

11 Claims, 5 Drawing Sheets

(56) References Cited

FOREIGN PATENT DOCUMENTS

| | | |
|---|---|---|
| JP | 44-31759 | 12/1969 |
| JP | 61-111677 A | 5/1986 |
| JP | 64-60364 A | 3/1989 |
| JP | 2-2331 A | 1/1990 |
| JP | 2-84166 A | 3/1990 |
| JP | 4-7749 A | 3/1992 |
| JP | 06-046821 A | 2/1994 |
| JP | 11-164679 A | 6/1999 |
| JP | 11-178562 A | 7/1999 |
| JP | 2001-95552 A | 4/2001 |
| JP | 2008-531008 A | 8/2008 |
| RU | 72821 U1 | 5/2008 |
| WO | 2006/090290 A1 | 8/2006 |

OTHER PUBLICATIONS

Takeda et al., "Effect of the Increase in the Permeability of Paper Materials for Cigarettes on the Pressure Drop and the Ventilation Rate of Filter Cigarettes," Japan TAPPI Journal, vol. 37, No. 8, Aug. 1983, pp. 37-46.

* cited by examiner

AMOUNT OF FILLER-FORMING
TOBACCO PARTICLES [g] (BY DRY BASIS)

NON-HEATING TOBACCO FLAVOR SUCTION DEVICE

CROSS REFERENCE TO RELATED APPLICATIONS

This application is a Continuation of PCT International Application No. PCT/JP2010/052369 filed on Feb. 17, 2010, which claims the benefit of Patent Application No. 2009-039380 filed in Japan, on Feb. 23, 2009. The entire content of all of the above applications is hereby incorporated by reference into the present application.

TECHNICAL FIELD

This invention relates to a non-heating tobacco flavor suction device which allows the user to enjoy inhaling a tobacco flavor without the need for ignition.

BACKGROUND ART

Filtered cigarettes have long been enjoyed as refreshing/relaxing articles. In recent years, however, the influence on the environment around of sidestream smoke and odor released from a burning filtered cigarette has been increasingly discussed.

In order to alleviate the problem, smokeless cigarettes, such as one disclosed in patent document 1, have been proposed.

The smokeless cigarette disclosed in patent document 1 comprises an air-permeable container filled with a filler formed of tobacco materials impregnated with flavoring substances derived from tobacco, including nicotine, and a holder for holding the container inside, the holder having an air intake and a mouth end. The user can enjoy a tobacco flavor by inhaling, through the mouth end, air having passed through the filler, without igniting the filler.

The smokeless cigarette disclosed in patent document 2 uses an air-permeable filler molded from tobacco powders and resin.

PRIOR-ART DOCUMENT

Patent document 1: Japanese Patent Application Laid-open No. Hei 2-2331 Publication
Patent document 2: Japanese Patent Application Laid-open No. Sho 64-60364 Publication

SUMMARY OF THE INVENTION

Problem to be Solved by the Invention

In the case of the smokeless cigarette disclosed in patent document 1, during inhaling, fine powders of tobacco materials are drawn toward the mouth end and gather near the mouth end, resulting in a rapid increase in the filler's ventilation resistance. This obstructs the user's inhaling tobacco-flavored air, so that the user cannot enjoy a flavor with a sensation similar to that which the user has when smoking ordinary filtered cigarettes.

The smokeless cigarette disclosed in patent document 2 does not have such drawback. However, the area of contact between air and tobacco powders is too small to allow the user to enjoy a satisfactory flavor. Further, filler molding requires resin, which leads to an increase in smokeless-cigarette production costs and man-hours.

An object of the present invention is to provide a non-heating tobacco flavor suction device which allows the user to inhale tobacco-flavored air and stably enjoy the flavor, without generating smoke.

Means for Solving the Problem

In order to achieve the above object, a non-heating tobacco flavor suction device comprises a hollow cylindrical suction holder having an open distal end, an open proximal end and a suction path defined inside, the suction path including a main passage extending from the distal end to the proximal end, the proximal end serving as a mouth end, and a filler contained in the main passage of the suction holder, the filer including tobacco particles made from tobacco materials to give a flavor deriving from the tobacco materials to air inhaled by a user through the mouth end, wherein the suction path and the filler provide a ventilation resistance of between about 40 and about 80 mmAq in cooperation with each other.

By controlling the ventilation resistance of the suction path and the filler between about 40 and about 80 mmAq, undesired movement of the filler-forming tobacco particles is prevented, and thus, local clogging of the filler due to agglomerated tobacco particles is prevented. The filler can therefore provide a stable sensation of inhaling and reliably give a flavor to air inhaled by the user.

The filler is easy to form, since it is formed by packing the tobacco particles without compressing the tobacco particles.

The filler is not burned, thus does not produce smoke or ash, and thus does not cause a problem such that smoke and odor worsen the environment around.

To keep the ventilation resistance of the suction path and the filler between about 40 and about 80 mmAq, it is desirable that the weight of the tobacco particles forming the filler is between 0.2 and 0.3 g by a dry basis.

Further, it is desirable that the filler includes 90 weight % or more of the tobacco particles, the tobacco particles having a particle size of between 0.212 and 2.0 mm.

It is more desirable that the filler includes 90 weight % or more of the tobacco particles, the tobacco particles having a particle size of between 0.5 and 2.0 mm.

It is desirable that the filler is cylindrical in shape and has an outside diameter of between 6 and 8 mm and an axial length of up to about 70 mm. The suction holder with such filler does not cause a feeling of strangeness as compared with ordinary filtered cigarettes.

The filler is easy to form, since it is formed without compression of the tobacco particles.

The tobacco particles include at least either carbonate or hydrogencarbonate, in which case flavoring substances contained in the tobacco materials are easily volatilized and released from the filler, so that the user can better enjoy the flavor deriving from the tobacco materials.

The carbonate is desirably potassium carbonate.

The suction path further includes a sub-passage for allowing air to be introduced into the main passage through a circumferential wall of the suction holder to cause the introduced air to come in contact with the filler. Such sub-passage can increase the amount of air taken into the suction holder, thereby diluting the to-be-inhaled flavored air.

Effect of the Invention

The present invention can prevent variations in the filler's ventilation resistance even with repetitive sucking actions, and allows the user to enjoy the flavor deriving from the tobacco materials with a sensation of inhaling similar to that which the user has when smoking ordinary filtered cigarettes.

BEST MODE OF CARRYING OUT THE INVENTION

Figure 1:
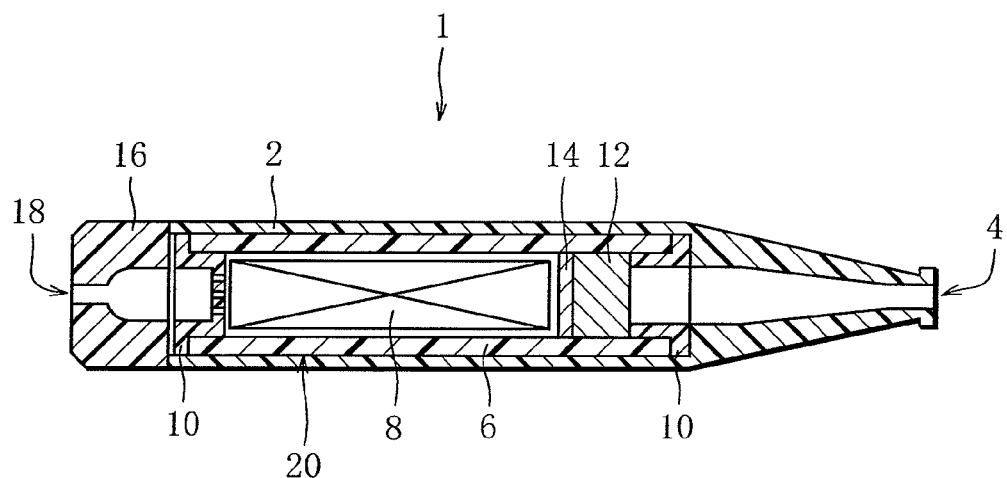
FIG. 1 is a cross-sectional view of a smokeless cigarette, or non-heating tobacco flavor suction device according to a first embodiment of the present invention.

As seen in FIG. 1, a smokeless cigarette 1 comprises a hollow cylindrical suction holder (hereinafter referred to simply as "holder") 2 similar in shape and size to ordinary filtered cigarettes. The holder 2 is open at either end. Specifically, the holder 2 includes a tapered proximal portion providing a mouth end 4.

Inside the holder 2, in a distal portion, a hollow cylindrical tobacco cartridge 20 is arranged. The tobacco cartridge 20 has an outside diameter somewhat smaller than the inside diameter of the distal portion of the holder 2, and is removable from the holder 2.

The tobacco cartridge 20 comprises a cylindrical container 6 open at either end, and a filler 8 arranged in the container 6. Air-permeable caps 10 are fitted to either end of the container 6. A filter 12 is fitted in the container 6, near the mouth end 4 side container 6 end. The filler 8 and the filter 12 are separated from each other by a filter stopper 14. The tobacco cartridge 20 is thus placed inside the holder 2 with the filter 12 side container 6 end toward the mouth end 4.

A cap 16 is removably fitted in the distal open end of the holder 2 remote from the mouth end 4. The cap 16 has an air intake 18.

The holder 2 has an air suction path for the air introduced into through the air intake 18 to flow. The suction path includes a main passage extending from the air intake 18 to the mouth end 4, inside the holder 2.

The filler 8 is formed by containing a mixture of tobacco shreds or grains, obtained by shredding or granulating tobacco leaves, and additives (such mixture will be hereinafter referred to as "tobacco particles"), in the container 6 so that the tobacco cartridge 20 will provide a predetermined ventilation resistance.

By the user's sucking action on the mouth end 4 of the holder 2, air is introduced into the tobacco cartridge 20, or in other words, the main passage, through the air intake 18, and contacts the filler 8, or tobacco particles. Thus, inside the cartridge 20, the air is given a tobacco flavor by containing flavoring substances released from the tobacco particles. The user can thus inhale the tobacco-flavored air, via the main passage and mouth end 4 of the holder 2, and enjoy the tobacco flavor.

In the case of the smokeless cigarette 1 not heating or burning the filler 8, the ventilation resistance of the filler 8 needs to be regulated appropriately in order that the smokeless cigarette 1 can not only give the user sensations similar to those given by smoking ordinary filtered cigarettes, but also overcome the aforementioned problem with the smokeless cigarette disclosed in patent document 1. In other words, the smokeless cigarette 1 according to the present invention needs to provide a stable flavor to the user and cause the user to feel an appropriate ventilation resistance during inhaling.

Table 1 below shows the length and the ventilation resistance of fillers formed of shreds in ordinary filtered cigarettes.

TABLE 1

| Type | Filler length [mm] | | Ventilation resistance [mmAq] | |
|---|---|---|---|---|
| | Before smoking | After smoking | Before smoking | After smoking |
| Filtered cigarette containing 1 mg tar | 51 | 10 | 104 | 101 |
| Filtered cigarette containing 6 mg tar | 53 | 10 | 100 | 82 |

As seen in Table 1, the ordinary filtered cigarettes are regulated such that, before ignition, the filler has an initial ventilation resistance of between about 100 and about 110 mmAq. In the filtered cigarettes smoked up to the filler length of about 10 mm, the filler's ventilation resistance is lower than the initial ventilation resistance. Specifically, after smoked up to the aforementioned filler length, the filtered cigarette containing 1 mg tar has a ventilation resistance (101 mmAq) slightly less than its initial ventilation resistance, and the filtered cigarette containing 6 mg tar has a ventilation resistance (82 mmAq) only 18 mmAq less than its initial ventilation resistance. This shows that, regardless of how much the filler length reduces by smoking, the ventilation resistance of ordinary filtered cigarettes is maintained between about 80 and about 100 mmAq.

The ventilation resistance is represented by a pressure loss measured under the standard filtered-cigarette smoking condition, or condition that the filtered-cigarette is sucked on at the flow rate of 1050 ml/min.

Table 2 below shows evaluations given by 16 testers who sucked on two types of smokeless cigarettes 1 different in ventilation resistance.

TABLE 2

| Ventilation resistances compared | Preference [Persons] | | | Sensibility of difference in ventilation resistance [Persons] | |
|---|---|---|---|---|---|
| A[mmAq] vs B[mmAq] | Prefer A | Prefer B | Express no preference | Perceived | Not perceived |
| 40 vs 60 | 4 | 5 | 7 | 9 | 7 |
| 60 vs 80 | 11 | 3 | 2 | 14 | 2 |
| 80 vs 100 | 10 | 2 | 4 | 12 | 4 |

In comparison between the smokeless cigarette 1 with ventilation resistance 40 mmAq and the smokeless cigarette 1 with ventilation resistance 60 mmAq, the testers' evaluations indicate that this difference in ventilation resistance is not a significant difference. By contrast, in comparison between the smokeless cigarette 1 with ventilation resistance 60 mmAq and the smokeless cigarette 1 with ventilation resistance 80 mmAq and between the smokeless cigarette 1 with ventilation resistance 80 mmAq and the smokeless cigarette 1 with ventilation resistance 100 mmAq, the testers' evaluations indicate that these differences in ventilation resistance are significant differences. It was also found that between the smokeless cigarettes 1 with respect to which the testers recognized a significant difference in ventilation resistance, the testers tended to prefer a smokeless cigarette 1 lower in ventilation resistance. Specifically, the test results show that the smokeless cigarette 1 with ventilation resistance 80 mmAq is preferred to the smokeless cigarette 1 with ventilation resistance 100 mmAq, and the smokeless cigarette 1 with ventilation resistance 60 mmAq is preferred to the smokeless cigarette 1 with ventilation resistance 80 mmAq, although there is recognized no definite testers' preference between the smokeless cigarette 1 with ventilation resistance 40 mmAq and the smokeless cigarette 1 with ventilation resistance 60 mmAq. The test results thus show that the ventilation resistance suitable for the smokeless cigarette 1 according to the present embodiment is different from that suitable for ordinary filtered cigarettes.

Table 2 also shows that in comparison between the smokeless cigarettes 1 different in ventilation resistance, a difference in ventilation resistance of about 20 mmAq or greater allows the testers' sensibility of the difference.

From the above, the ventilation resistance suitable for the smokeless cigarette 1 according to the present embodiment is 80 mmAq or below, more specifically between about 40 and about 80 mmAq. The ventilation resistance of the smokeless cigarette 1, or tobacco cartridge 20 is the sum of ventilation resistances of the filler 8, the caps 10 and the filter 12. If the ventilation resistances of the caps 10 and the filter 12 are, for example 2 mmAq and 15 mmAq, respectively, the filler 8 must have a ventilation resistance of between 23 and 63 mmAq.

The ventilation resistance of the filler 8, which needs to be appropriately regulated, is greatly affected by the amount and the particle size of tobacco particles that form the filler 8. Next, the amount and the particle size of the filler-forming tobacco particles will be further discussed.

Figure 2:
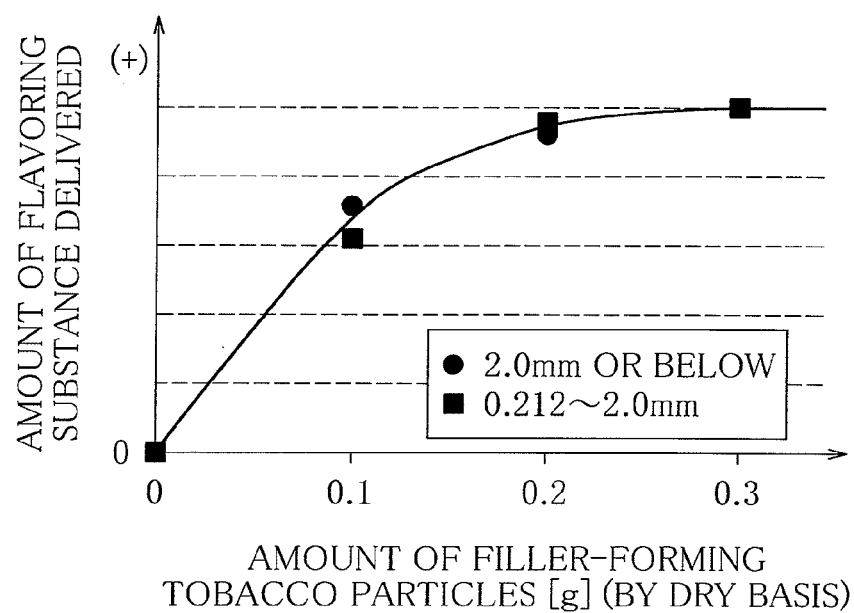
FIG. 2 is a graph showing relation between the amount of tobacco particles forming a filler shown in FIG. 1 and the amount of a tobacco flavoring substance delivered.

FIG. 2 shows relation between the amount of a flavoring substance delivered from the smokeless cigarette 1 per puff and the amount of filler-forming tobacco particles (by a dry basis). The flavoring substance here is a substance chosen from the flavoring substances contained in the tobacco particles as an indicator of a tobacco flavor (specifically, nicotine).

The specifications of the filler 8 for which the relation shown in FIG. 2 was observed are as follows:

Tobacco particles: a mixture of burley-tobacco shreds, obtained by subjecting burley leaves to shredding, humidification and then heating, and additives such as carbonate (potassium carbonate) and flavorings Particle size of 90 weight % or more of filler-forming tobacco particles: between 0.212 and 2.0 mm Outside diameter (inside diameter of the tobacco cartridge): 7 mm As seen in FIG. 2, the delivery of the flavoring substance increases as the filler-forming tobacco particles increase, but reaches a constant value at 0.3 g of filler-forming tobacco particles. Further, the filler 8 formed of 0.2 g or more of tobacco particles delivers substantially the same amount of the flavoring substance as the filler formed of 0.3 g of tobacco particles delivers. It is therefore desirable that the filler 8 be formed of between 0.2 and 0.3 g of tobacco particles by the dry basis.

Addition of carbonate, such as potassium carbonate, to the tobacco particles leads to a "rich" tobacco flavor and an improved sensation of tobacco-flavored air inhaling, and thus, enhanced user satisfaction. Potassium carbonate in powder form may be mixed with the tobacco particles. Alternatively, an aqueous solution of potassium carbonate may be added to the tobacco particles. Hydrogencarbonate may be used in place of or in addition to carbonate.

Table 3 below shows relation between the initial ventilation resistance of the tobacco cartridge 20 and the particle size of filler 8 forming tobacco particles.

TABLE 3

| | Initial ventilation resistance [mmAq] | |
|---|---|---|
| Particle size (90 weight % or more) | Amount of filler-forming tobacco particles: 0.2 [g] (by dry basis) | Amount of filler-forming tobacco particles: 0.3 [g] (by dry basis) |
| 2.0 mm or below | 60 | 99 |
| 0.212~2.0 mm | 58 | 79 |

The type and the amount of filler 8 forming tobacco particles and the outside diameter of the filler 8, for which the relation shown in Table 3 was observed, are the same as mentioned above.

As seen in Table 3, a tobacco cartridge 20 containing a filler 8 formed of 0.3 g of tobacco particles with a particle size of 2.0 mm or below has an initial ventilation resistance of 99 mmAq, which is outside the aforementioned ventilation-resistance range suitable for the smokeless cigarette 1. By contrast, a tobacco cartridge 20 containing a filler 8 formed of 0.2 g or 0.3 g of tobacco particles with a particle size of between 0.212 and 2.0 mm provides an initial ventilation resistance within the aforementioned suitable ventilation-resistance range.

It is therefore desirable that 90 weight % or more of the tobacco particles that form the filler 8 have a particle size of between 0.212 and 2.0 mm. Tobacco particles with a particle size of between 0.212 and 2.0 mm are obtained by sieving by means of a standard sieve with a mesh size according to JISZ8801.

Table 4 below shows how the particle size of tobacco particles relates to the initial ventilation resistance of the tobacco cartridge 20, the terminal ventilation resistance after 100 puffs of the tobacco cartridge 20, and the difference between the initial and terminal ventilation resistances.

TABLE 4

| | Ventilation resistance [mmAq] with a filler formed of 0.2 [g] of tobacco particles (by dry basis) | | | Ventilation resistance [mmAq] with a filler formed of 0.3 [g] of tobacco particles (by dry basis) | | |
|---|---|---|---|---|---|---|
| Particle size of 90 weight % or more of tobacco particles | Initial | Terminal | Difference | Initial | Terminal | Difference |
| 2.0 mm or below | 60 | 86 | 26 | 99 | 136 | 37 |
| 0.212~2.0 mm | 58 | 71 | 13 | 79 | 99 | 20 |
| 0.5~2.0 mm | 57 | 65 | 8 | 72 | 81 | 9 |

The specifications of the filler 8 for which the relation shown in Table 4 was observed are the same as given above.

As seen in Table 4, a tobacco cartridge 20 containing a filler formed of 0.2 g of tobacco particles provides an initial and terminal ventilation resistances each within the aforementioned range of between 40 and 80 mmAq, if the tobacco particles have a particle size of between 0.212 and 2.0 mm or between 0.5 and 2.0 mm. If, however, the tobacco particles have a particle size of 2.0 mm or below, such tobacco cartridge 20 has a terminal ventilation resistance of 86 mmAq, which is outside the aforementioned suitable ventilation-resistance range.

A tobacco cartridge 20 containing a filler formed of 0.3 g of tobacco particles has an initial and terminal ventilation resistances each outside the aforementioned suitable ventilation-resistance range, if the tobacco particles have a particle size of 2.0 mm or below. If the tobacco particles have a particle size of between 0.212 and 2.0 mm, such tobacco cartridge 20 provides a terminal ventilation resistance outside the aforementioned suitable ventilation-resistance range, but if the tobacco particles have a particle size of between 0.5 and 2.0 mm, such tobacco cartridge 20 provides a terminal ventilation resistance practically in the aforementioned suitable ventilation-resistance range.

In addition, if the tobacco particles have a particle size of 2.0 mm or below, the tobacco cartridge 20 has a difference between the initial and terminal ventilation resistances of 20 mm Aq or greater, which is great enough to cause the user to be clearly aware of a variation in ventilation resistance of the tobacco cartridge 20, and thus, have a feeling of strangeness during use of the smokeless cigarette 1.

The particle size of the tobacco particles forming the filler 8 is therefore desirably between 0.212 and 2.0 mm, and more desirably between 0.5 and 2.0 mm.

Table 5 below shows mutual relation between the filler 8's outside diameter (tobacco cartridge 20's inside diameter), the filler 8's length, and the initial ventilation resistance of the tobacco cartridge 20.

TABLE 5

| Filler outside diameter [mm] | Amount of filler-forming tobacco particles 0.2 [g] (by dry basis) | | Amount of filler-forming tobacco particles 0.3 [g] (by dry basis) | |
|---|---|---|---|---|
| | Filler length [mm] | Initial ventilation resistance [mmAq] | Filler length [mm] | Initial ventilation resistance [mmAq] |
| φ5 | 91 | 96 | 135 | 120 |
| φ7 | 46 | 57 | 69 | 72 |
| φ8 | 36 | 31 | 53 | 38 |
| φ9 | 28 | 10 | 42 | 16 |

Except for the outside diameter, the specifications of the filler 8 for which the relation shown in Table 5 was observed are the same as given above, and the particle size of the filler 8 forming tobacco particles is between 0.5 and 2.0 mm.

As seen in table 5, the length and the outside diameter of the filler 8 depend on the amount of filler-forming tobacco particles. For example, the length of the filler 8 of outside diameter 5 mm measures as great as 91 mm (0.2 g of filler-forming tobacco particles) or 135 mm (0.3 g of filler-forming tobacco particles). Such filler 8 is much longer than the filler part of ordinary filtered cigarettes, which measures between about 59 and about 68 mm. In addition, the tobacco cartridge 20 containing such filler has an initial ventilation resistance outside the aforementioned suitable ventilation-resistance range. The tobacco cartridge 20 containing the filler 8 of outside diameter 5 mm, therefore, causes to the user a feeling of strangeness, and thus is not usable.

The tobacco cartridge 20 containing a filler 8 of outside diameter 7 mm provides an initial ventilation resistance within the aforementioned suitable ventilation-resistance range, whether the filler is formed of 0.2 g or 0.3 g of tobacco particles. The tobacco cartridge 20 containing a filler 8 of outside diameter 8 mm provides an initial ventilation resistance slightly below the aforementioned suitable ventilation-resistance range, whether the filler is formed of 0.2 g or 0.3 g of tobacco particles. In addition, the filler 8 of outside diameter 7 mm or 8 mm has a length nearly equal to or less than the length of the filler part of ordinary filtered cigarettes.

The tobacco cartridge 20 containing a filler 8 of outside diameter 9 mm has an initial ventilation resistance of 10 mmAq (0.2 g of filler-forming tobacco particles) or 16 mmAq (0.3 g of filler-forming tobacco particles) far outside the aforementioned suitable ventilation-resistance range, and thus is not suitable for use.

Consequently, the outside diameter of the filler 8 (inside diameter of the tobacco cartridge 20) is desirably between 6 and 8 mm, and the length of the filler 8 is desirably nearly equal to or less than the length of the filler part of ordinary filtered cigarettes, specifically up to about 70 mm.

Table 6 below shows mutual relation between the degree of compression, or how much the tobacco particles are compressed to form the filler 8, the filler length, and the initial ventilation resistance of the tobacco cartridge 20.

TABLE 6

| Compression [%] | Filler length [mm] | Initial ventilation resistance [mmAq] |
|---|---|---|
| 0 | 69 | 72 |
| 5 | 65 | 99 |
| 20 | 55 | 145 |

The specifications of the filler 8 for which the relation shown in Table 6 was observed are the same as given above. Specifically, the filler 8 is formed of 0.3 g of tobacco particles by the dry basis, and measures 7 mm in outside diameter.

As shown in Table 6, 0% compression means that the filler 8 in the tobacco cartridge 20 is not compressed, or has no load exerted on, in which case the filler 8 measures 69 mm in length and the tobacco cartridge 20 provides an initial ventilation resistance of 72 mmAq within the aforementioned suitable ventilation-resistance range.

5% and 20% compressions mean that the filler 8 with no load exerted on has been compressed up to the length of about 65 mm and 55 mm, respectively, in which cases the tobacco cartridge 20 has initial ventilation resistances of 99 mmAq and 145 mmAq, respectively, outside the aforementioned suitable ventilation-resistance range.

Thus, when forming a filler 8 by containing tobacco particles in the tobacco cartridge 20, the tobacco particles do not need to be compressed. The filler 8 is therefore easy to form.

From the above, it is concluded that, provided that at least either the amount or the particle size of the filler-forming tobacco particles is chosen from the aforementioned range of values resulting in the tobacco cartridge 20 ventilation resistance of between 40 and 80 mmAq, the filler 8 can stably release tobacco flavoring substances. The smokeless cigarette 1 according to the present embodiment thus allows the user to enjoy a flavor and a sensation of inhaling similar to those provided by ordinary filtered cigarettes.

The filler 8 is not burned, thus does not produce smoke or ash, and thus does not cause such problem that smoke and odor worsen the environment around.

The present invention is not restricted to the above-described first embodiment, but can be altered in various ways without departing from the scope and spirit thereof.

Figure 3:
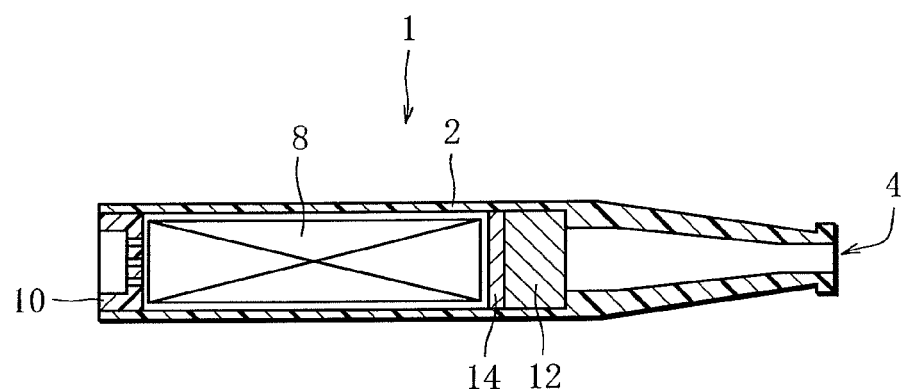
FIG. 3 is a cross-sectional view of a smokeless cigarette according to a second embodiment.

For example, while the smokeless cigarette 1 according to the first embodiment has a tobacco cartridge 20 with a filler 8 held in a container 6, a smokeless cigarette 1 according to a second embodiment has a filler 8 directly held inside the holder 2, as shown in FIG. 3. The smokeless cigarette 1 according to the second embodiment is a disposable, or single-use smokeless cigarette.

The holder 2 may have an air intake 18, for example at the circumference, in addition to that at the distal end. This renders the circumferential wall of the container 6 air-permeable.

Figure 4:
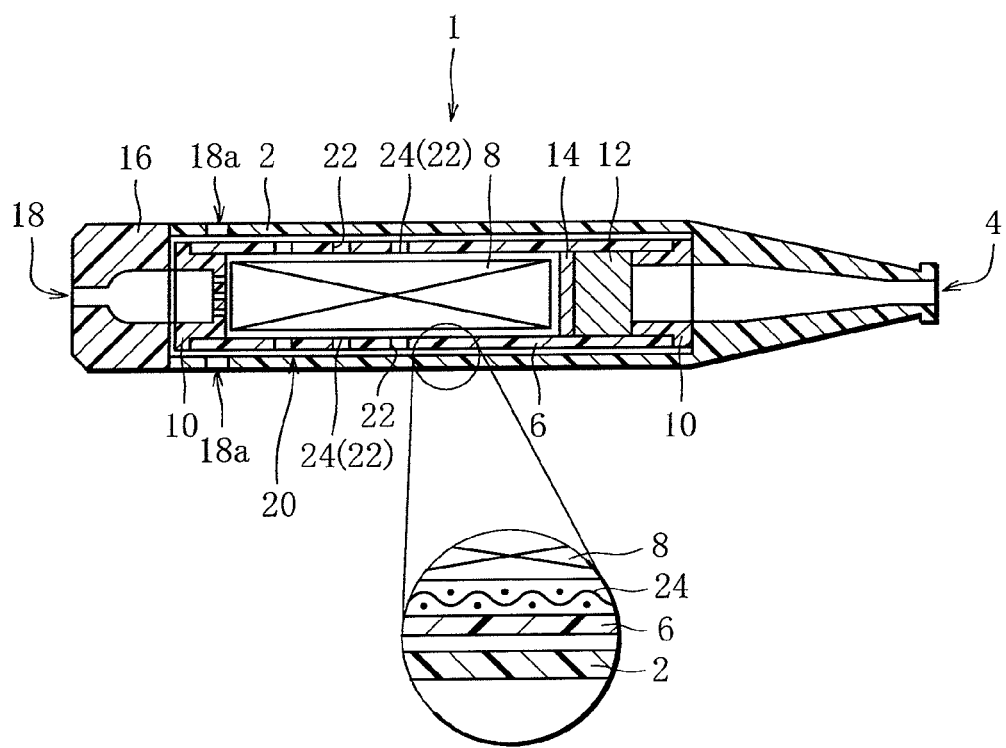
FIG. 4 is a cross-sectional view of a smokeless cigarette according to a third embodiment.

Specifically, the third embodiment shown in FIG. 4 has a plurality of air intakes 18a in the circumferential wall of the holder 2, near the distal end thereof, in addition to the air intake 18 at the distal end. The air intakes 18a are disposed in the direction of circumference of the holder 2 at intervals. In addition, the circumferential wall of the container 6 has a lot of ventilation holes 22 distributed downstream of the air intakes 18a, which render the circumferential wall of the container 6 air-permeable. An annular space of a predetermined size is left between the holder 2 and the container 6 to provide a sub-passage connecting the air intakes 18a and the ventilations holes 22. In order to prevent tobacco particles from dropping through the ventilation holes 22, a mesh net 24 is attached to the inner surface of the container 6.

Air introduced into the holder 2 through the air intakes 18a flows in the sub-passage, or space between the inner surface of the holder 2 and the outer surface of the container 6, entering the ventilation holes 22 in the container 6 and the meshes in the mesh net 24, radially with respect to the container 6, and thus contacting with the tobacco particles forming the filler 8. Such radial flows of air do not push on the tobacco particles in the container 6 in the direction of axis of the container 6. Thus, the problem that the tobacco particles in the container 6 move toward the filter 12 side end of the container 6 and agglomerate together can be avoided and a desired ventilation resistance can be maintained, which allows the user to inhale tobacco flavoring substances more stably.

The smokeless cigarette 1 may be provided with only one air intake 18a and only one ventilation hole 22.

An openable lid, for example a slide lid may be provided to close the air intakes 18a. Such slide lid enables regulation of the amount of air introduced into the holder 2. If the user feels that the flavor given by the filler 8 is too strong, the user can operate the slide lid to increase the amount of air introduced into the holder 2 through the air intakes 18a, thereby diluting the to-be-inhaled flavored air.

Figure 5:
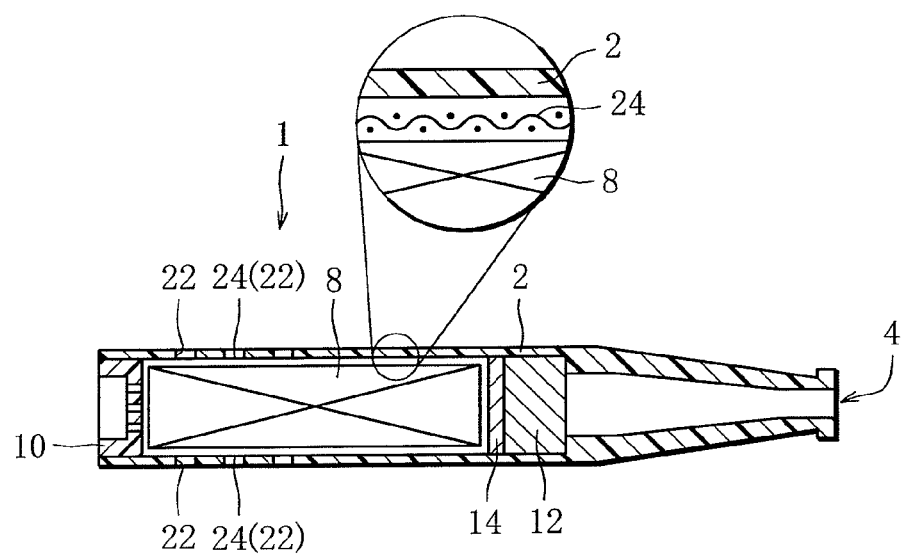
FIG. 5 is a cross-sectional view of a smokeless cigarette according to a fourth embodiment.

The smokeless cigarette 1 according to a fourth embodiment shown in FIG. 5 is a disposable smokeless cigarette, as the smokeless cigarette 1 shown in FIG. 3 is, but has a plurality of ventilation holes 22 in the circumferential wall of the holder 2 and a mesh net 24 attached to the inner surface of the holder 2.

Figure 6:
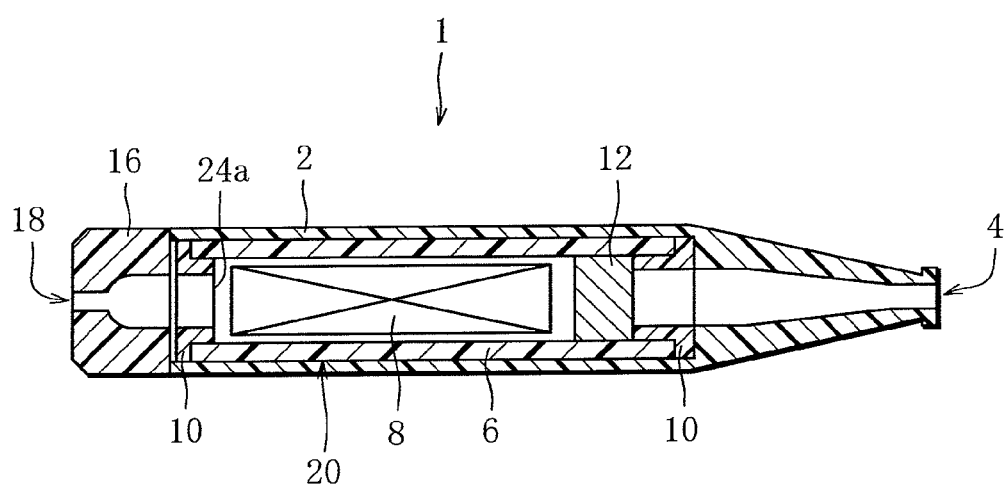
FIG. 6 is a cross-sectional view of a smokeless cigarette according to a fifth embodiment.

The smokeless cigarette 1 according to a fifth embodiment shown in FIG. 6 differs from the smokeless cigarette 1 shown in FIG. 1 only in that the filter stopper 14 is omitted and the distal end side cap 10 includes a mesh net 24a which renders it air-permeable.

Figure 7:
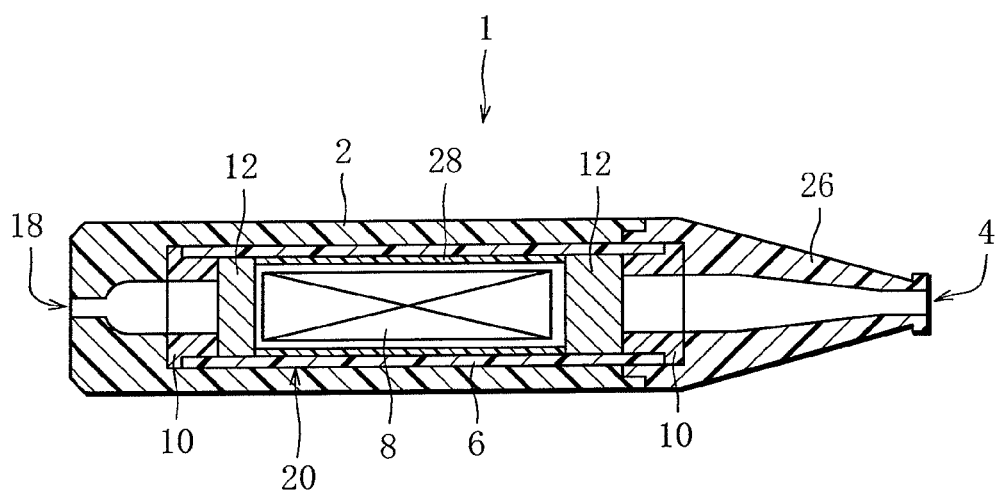
FIG. 7 is a cross-sectional view of a smokeless cigarette according to a sixth embodiment.

The smokeless cigarette 1 according to a sixth embodiment shown in FIG. 7 has a mouth piece 26 providing a mouth end 4, removably attached to the holder 2, and filters 12 provided at either end of the container 6.

Figure 8:
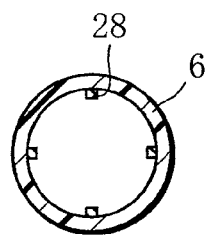
FIG. 8 is a cross-sectional view of a container in the smokeless cigarette according to the sixth embodiment.

In addition, the smokeless cigarette 1 according to the sixth embodiment has a plurality of ribs 28 on the inner surface of the container 6. The ribs 28 each extend in the direction of axis of the container 6, between the filters 12. As seen in FIG. 8, the ribs 28 are disposed in the direction of circumference of the container 6 at intervals. These ribs 28 are useful in preventing the filters 12 from moving toward the filler 8 in the container 6.

Figure 9:
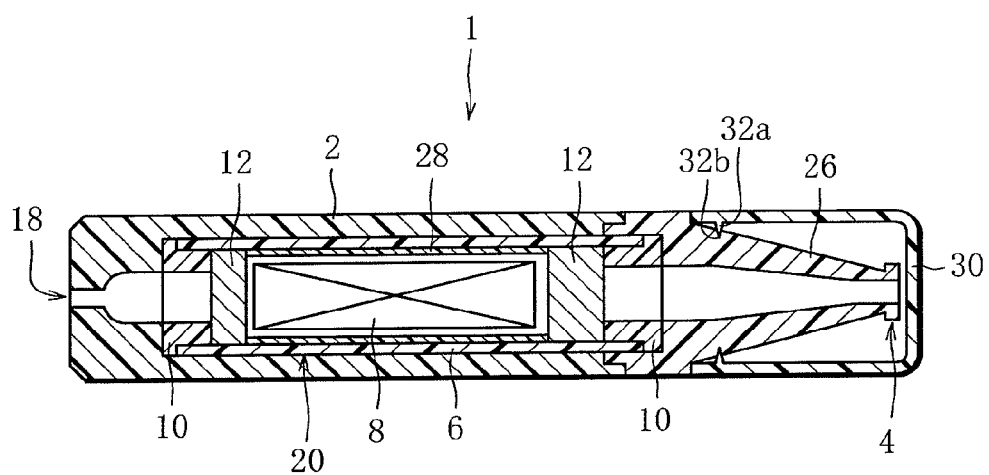
FIG. 9 is a cross-sectional view of a smokeless cigarette according to a seventh embodiment.

The smokeless cigarette 1 according to a seventh embodiment shown in FIG. 9 further comprises a cylindrical mouth-end cap 30 covering the mouth end 4. The mouth-end cap 30 has an open end having an outside diameter equal to that of the holder 2. The mouth-end cap has a pair of projections 32a on the inner surface, near the open end. The projections 32a face each other with the axis of the mouth-end cap 30 interposed between. The projections 32a can engage with the mouth end 4 portion, specifically with recesses 32b in the outer circumferential surface of the mouth-end piece 30. The mouth-end cap 30 is thus removably attached to cover the mouth piece 26 to prevent adhesion of dirt to the mouth piece 26 during storage of the smokeless cigarette 1.

EXPLANATION OF REFERENCE CHARACTERS

1: Smokeless cigarette
2: Holder
4: Mouth end (main passage)
6: Container
8: Filler
10: Cap
12: Filter
14: Filter stopper
16: Cap
18: Air intake (main passage)
18a: Air intake (sub-passage)
20: Tobacco cartridge
22: Ventilation hole (sub-passage)
24, 24a: Mesh net
26: Mouth piece
28: Rib
30: Mouth-end cap
32a: Recess
32b: Projection

The invention claimed is:

1. A non-heating tobacco flavor suction device, comprising:
a hollow, cylindrical suction holder made of a synthetic resin and having an open distal end, an open proximal end and a suction path defined therebetween, the suction path including a main passage extending from the distal end to the proximal end, the proximal end serving as a tapered mouth end, and
a filler contained in the main passage of said suction holder, said filler, including tobacco particles made from tobacco materials, potassium carbonate and a hydrogen carbonate, without compressing the tobacco particles, to give in the absence of heating, a flavor derived from the tobacco materials to the air inhaled by a user through the mouth end,
wherein the tobacco particles have a particle size of between 0.212 and 2.0 mm and
wherein a filling amount of the tobacco particles in said filler is set such that said filler exhibits the following features (i) and (ii):

(i) said filler provides an initial ventilation resistance before said tobacco flavor suction device is first sucked, and provides a terminal ventilation resistance greater than the initial ventilation resistance after said tobacco flavor suction device is repeatedly sucked, said terminal ventilation resistance being the ventilation resistance observed after 100 puffs of the tobacco flavor suction device; and (ii) the initial and terminal ventilation resistances are each within a range of between about 40 mmAq and about 80 mmAq, and the difference between the initial and terminal ventilation resistances is smaller than 20 mmAq.

2. The non-heating tobacco flavor suction device according to claim 1, wherein the weight of the tobacco particles forming said filler is between 0.2 and 0.3 g by a dry basis.

3. The non-heating tobacco flavor suction device according to claim 1, wherein said filler includes 90 weight % or more of the tobacco particles.

4. The non-heating tobacco flavor suction device according to claim 1, wherein said filler includes 90 weight % or more of the tobacco particles, the tobacco particles having a particle size of between 0.5 and 2.0 mm.

5. The non-heating tobacco flavor suction device according to claim 1, wherein said filler is cylindrical in shape and has an outside diameter of between 6 and 8 mm and an axial length of up to about 70 mm.

6. The non-heating tobacco flavor suction device according to claim 1, wherein the suction path further includes a sub-passage for allowing air to be introduced into the main passage through a circumferential wall of said suction holder to cause the introduced air to come in contact with said filler.

7. The non-heating tobacco flavor suction device according to claim 1, wherein the suction device further comprises a hollow tobacco cartridge container removably arranged in said suction holder, said tobacco cartridge container forming a part of the main passage and including said filler therein.

8. The non-heating tobacco flavor suction device according to claim 7, wherein said tobacco cartridge container further includes air-permeable caps fitted to either end thereof.

9. The non-heating tobacco flavor suction device according to claim 8, wherein the suction path further includes a sub-passage for allowing air to be introduced into the main passage through circumferential walls of said suction holder and tobacco cartridge to cause the introduced air to come in contact with said filler.

10. The non-heating tobacco flavor suction device according to claim 9, wherein said tobacco cartridge further includes a mesh net attached to an inner surface thereof.

11. A non-heating tobacco flavor suction device which consists essentially of a hollow, cylindrical suction holder made of a synthetic resin and having an open distal end, an open proximal end and a suction path defined therebetween, the suction path including a main passage extending from the distal end to the proximal end, the proximal end serving as a tapered mouth end, and a filler contained in the main passage of said suction holder, said filler, including tobacco particles made from tobacco materials, potassium carbonate and a hydrogen carbonate, without compressing the tobacco particles, to give in the absence of heating, a flavor derived from the tobacco materials to the air inhaled by a user through the mouth end, wherein the tobacco particles have a particle size of between 0.212 and 2.0 mm and wherein a filling amount of the tobacco particles in said filler is set such that said filler exhibits the following features (i) and (ii):

(i) said filler provides an initial ventilation resistance before said tobacco flavor suction device is first sucked, and provides a terminal ventilation resistance greater than the initial ventilation resistance after said tobacco flavor suction device is repeatedly sucked, said terminal ventilation resistance being the ventilation resistance observed after 100 puffs of the tobacco flavor suction device; and (ii) the initial and terminal ventilation resistances are each within a range of between about 40 mmAq and about 80 mmAq, and the difference between the initial and terminal ventilation resistances is smaller than 20 mmAq, and wherein the non-heating tobacco flavor suction device allows a user to enjoy inhaling the tobacco flavor without the need for ignition.

* * * * *